US006897323B2

(12) United States Patent
Boaz et al.

(10) Patent No.: US 6,897,323 B2
(45) Date of Patent: May 24, 2005

(54) HIGHLY ENANTIOMERICALLY PURE LACTAM-SUBSTITUTED PROPANOIC ACID DERIVATIVES AND METHODS OF MAKING AND USING SAME

(75) Inventors: Neil Warren Boaz, Kingsport, TN (US); Sheryl Davis Debenham, Scotch Plains, NJ (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/722,283

(22) Filed: Nov. 25, 2003

(65) Prior Publication Data

US 2004/0106788 A1 Jun. 3, 2004

Related U.S. Application Data

(62) Division of application No. 09/957,182, filed on Sep. 20, 2001, now Pat. No. 6,686,477.
(60) Provisional application No. 60/236,564, filed on Sep. 29, 2000, and provisional application No. 60/264,411, filed on Jan. 26, 2001.

(51) Int. Cl.$^7$ ..................... C07D 207/12; C07D 207/24
(52) U.S. Cl. ..................................... 548/550; 548/551
(58) Field of Search ................................. 548/550, 551

(56) References Cited

U.S. PATENT DOCUMENTS

| | | | | |
|---|---|---|---|---|
| 3,022,293 A | * | 2/1962 | Miller | 260/239.3 |
| 4,108,992 A | | 8/1978 | Pearson et al. | |
| 4,446,146 A | | 5/1984 | Southgate et al. | |
| 4,552,889 A | * | 11/1985 | Scott | 514/424 |
| 4,696,943 A | | 9/1987 | Gobert et al. | |

FOREIGN PATENT DOCUMENTS

| | | |
|---|---|---|
| DE | 19918420 | 10/2000 |
| EP | 0 106 988 | 5/1984 |
| EP | 0 306 266 | 3/1989 |
| EP | 0 365 992 | 5/1990 |
| GB | 1 309 692 | 3/1973 |
| GB | 2110207 | 6/1983 |
| GB | 2202075 | 9/1988 |
| JP | 10279541 | 10/1998 |
| WO | WO 92 16497 | 10/1992 |
| WO | WO 96 17862 | 6/1996 |
| WO | WO 97 40809 | 11/1997 |
| WO | WO 01 62726 | 8/2001 |

OTHER PUBLICATIONS

Easton et al., Tetrahedron Letters (1990), 31 24, 3471–4.*
Ohkuma et al. "Catalytic Asymmetric Synthesis," 2nd Ed. Wiley–VCH, Inc., pp. 1–17 (2000).
Zoller et al. "Amidoalkylation of Mercaptans With Glyoxylic Acid Derivatives" Tetrahedron, vol. 31:pp. 863–866 (1975).
Schmidt et al. Amino Acids and Peptides; XLIII, Dehydroamino Acids; XVIII, Synthesis of Dehydroamino Acids and Amino Acids from N–Acyl–2–(dialkyloxyphosphinyl)–glycin Esters; II Synthesis, pp. 53–60, Jan. 1984.
Richards et al, Tetrahedron: Asymmetry, 1998, vol. 9, pp. 2377–2407.
Fiorini et al, Journal of Molecular Catalysis, 1979, vol. 5, pp. 303–310.
Pracejus et al, Tetrahedron Letters, 1977, vol. 39, pp. 3497–3500.
Marquarding et al, Journal of the American Chemical Society, 1970, vol. 92, pp. 5389–5393.
Armstrong et al, Analytical Chemistry, 1985, vol. 57, No. 2, pp. 481–484.
Boaz, Tetrahedron Letters, 1989, vol. 30, No. 16, pp. 2061–2064.
Hayashi et al, Bull Chemical Society of Japan, 1980, vol. 53, No. 4, pp. 1138–1151.
Schmidt et al, Synthesis, 1992, pp. 487–490.
Katritzky et al, Journal of Organic Chemistry, 2000, vol. 65, pp. 4364–4369.
Lloyd et al, Tetrahedron, 1999, vol. 55, No. 33, pp. 10201–10220.
Nicolas et al, Drug Metabolism and Disposition, 1999, vol. 27, No. 2, pp. 250–254.
Wolfe et al, Journal of Organic Chemistry, 1997, vol. 62, pp. 654–663.
Kim et al., Bulletin of the Korean Chemical Society, 1996, vol. 17, No. 1, pp. 34–38.
Noyer et al, European Journal of Pharmacology, 1995, vol. 286, No. 2, pp. 137–146.
Baggaley et al, Journal of The Chemical Society, 1990, vol. 6, pp. 1521–1533.
Thaisrivongs et al, Journal of Medicinal Chemistry, 1988, vol. 31, No. 7, pp. 1369–1376.
Shipov et al, Journal of General Chemistry of the U.S.S.R., 1991, pp. 2142–2150.
Roth et al, Tetrahedron, 1995, vol. 51, No. 3, pp. 801–810.

* cited by examiner

*Primary Examiner*—Bruck Kifle
(74) *Attorney, Agent, or Firm*—Michael J. Blake; Bernard J. Graves, Jr.

(57) ABSTRACT

The present invention relates to highly enantiomerically pure lactam-substituted propanoic acid derivatives and methods of making and using therefor. The invention involves a multi-step synthesis to produce the lactam compounds. In one step of the reaction sequence, asymmetric hydrogenation of a lactam-enamide was performed to produce an intermediate that can ultimately be converted to a series of pharmaceutical compounds. The invention also contemplates the in situ synthesis of an intermediate of the multi-step synthesis, which provides economic advantages to the overall synthesis of the lactam compounds.

10 Claims, No Drawings

HIGHLY ENANTIOMERICALLY PURE LACTAM-SUBSTITUTED PROPANOIC ACID DERIVATIVES AND METHODS OF MAKING AND USING SAME

CROSS REFERENCE TO RELATED APPLICATIONS

This application is a divisional application of Nonprovisional Application Ser. No. 09/957,182, filed Sep. 20, 2001, and now issued as U.S. Pat. No. 6,686,477, which claims priority to U.S. Provisional Application Nos. 60/236,564, filed Sep. 29, 2000, and 60/264,411, filed Jan. 26, 2001, both entitled "Phosphino-Aminophosphines," which applications are hereby incorporated by this reference in their entireties.

BACKGROUND OF THE INVENTION

Asymmetric catalysis is the most efficient method for the generation of products with high enantiomeric purity, as the asymmetry of the catalyst is multiplied many times over in the generation of the chiral product. These chiral products have found numerous applications as building blocks for single enantiomer pharmaceuticals as well as in some agrochemicals. The asymmetric catalysts employed can be enzymatic or synthetic in nature. The latter types of catalyst have much greater promise than the former due to much greater latitude of applicable reaction types. Synthetic asymmetric catalysts are usually composed of a metal reaction center surrounded by an organic ligand. The ligand usually is generated in high enantiomeric purity, and is the agent inducing the asymmetry. A prototypical reaction using these types of catalyst is the asymmetric hydrogenation of enamides to afford amino-acid derivatives (Ohkuma, T.; Kitamura, M.; Noyori, R. In *Catalytic Asymmetric Synthesis,* 2nd ed.; Ojima, I., Ed.; Wiley-VCH: New York, 2000; pp. 1–17).

Although the preparation of enamides through Horner-Emmons Wittig chemistry is known, the preparation and use of substrates such as lactam-substituted 2-propenoic acid derivatives which possess a fully substituted nitrogen on the enamide are not known and the viability of the standard preparative sequence for the enamide is unclear. In general, the majority of enamides that have undergone asymmetric hydrogenation possess a hydrogen substituent on the nitrogen of the enamide. Thus the efficacy of asymmetric catalysts for the hydrogenation of lactam-substituted 2-propenoic acid derivatives is also unclear.

U.S. Pat. No. 4,696,943 discloses the synthesis of single enantiomer lactam-substituted propanoic acid derivatives useful as pharmaceutical agents for various conditions. However, these compounds were prepared by a cyclization reaction and not by the asymmetric hydrogenation of an enamide.

In light of the above, it would be desirable to produce single enantiomer lactam-substituted propanoic acid derivatives useful as pharmaceutical compounds.

SUMMARY OF THE INVENTION

The present invention relates to highly enantiomerically pure lactam-substituted propanoic acid derivatives and methods of making and using therefor. The invention involves a multi-step synthesis to produce the lactam compounds. In one step of the reaction sequence, asymmetric hydrogenation of a lactam-enamide was performed to produce an intermediate that can ultimately be converted to a series of pharmaceutical compounds. The invention also contemplates the in situ synthesis of an intermediate of the multi-step synthesis, which provides economic advantages to the overall synthesis of the lactam compounds.

Additional advantages of the invention will be set forth in part in the description that follows, and in part will be apparent from the description or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of aspects of the invention and the Examples included therein.

Before the present compositions of matter and methods are disclosed and described, it is to be understood that this invention is not limited to specific synthetic methods or to particular formulations, and, as such, may, of course, vary. It is also to be understood that the terminology used herein is for the purpose of describing particular aspects only and is not intended to be limiting.

The singular forms a, an, and the include plural referents unless the context clearly dictates otherwise.

Optional or optionally means that the subsequently described event or circumstances may or may not occur, and that the description included instances where said event or circumstance occurs and instances where it does not.

The term "alkyl group" may include straight- or branched-chain, aliphatic hydrocarbon radicals containing up to about 20 carbon atoms and may be substituted, for example, with one to three groups selected from $C_1$–$C_6$-alkoxy, cyano, $C_2$–$C_6$-alkoxycarbonyl, $C_2$–$C_6$ alkanoyloxy, hydroxy, aryl and halogen. The terms "$C_1$–$C_6$-alkoxy," "$C_2$–$C_6$-alkoxycarbonyl," and "$C_2$–$C_6$-alkanoyloxy" are used to denote radicals corresponding to the structures —OR, —$CO_2$R, and —OCOR, respectively, wherein R is $C_1$–$C_6$-alkyl or substituted $C_1$–$C_6$-alkyl.

The term "cycloalkyl" is used to denote a saturated, carbocyclic hydrocarbon. The term "substituted cycloalkyl" is a cycloalkyl group substituted with one or more of the groups described above.

The term "aryl group" may include phenyl, naphthyl, or anthracenyl and phenyl, naphthyl, or anthracenyl substituted with one to three substituents selected from $C_1$–$C_6$-alkyl, substituted $C_1$–$C_6$-alkyl, $C_6$–$C_{10}$ aryl, substituted $C_6$–$C_{10}$ aryl, $C_1$–$C_6$-alkoxy, halogen, carboxy, cyano, $C_1$–$C_6$-alkanoyloxy, $C_1$–$C_6$-alkylthio, $C_1$–$C_6$-alkylsulfonyl, trifluoromethyl, hydroxy, $C_2$–$C_6$-alkoxycarbonyl, $C_2$–$C_6$-alkanoylamino and —OR', SR', —$SO_2$R', —$NHSO_2$R' and —$NHCO_2$R', wherein R' is phenyl, naphthyl, or phenyl or naphthly substituted with one to three groups selected from $C_1$–$C_6$-alkyl, $C_6$–$C_{10}$ aryl, $C_1$–$C_6$-alkoxy and halogen.

The term "heteroaryl group" includes a 5- or 6- membered aromatic ring containing one to three heteroatoms selected from oxygen, sulfur and nitrogen. Examples of such heteroaryl groups are thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridyl, pyrimidyl, benzoxazolyl, benzothiazolyl, benzimidazolyl, indolyl and the like. The heteroaryl group may be substituted, for example, with up to three groups such as $C_1$–$C_6$-alkyl, $C_1$–$C_6$-alkoxy, substituted $C_1$–$C_6$-alkyl, halogen, $C_1$–$C_6$-alkylthio, aryl, arylthio, aryloxy, $C_2$–$C_6$-alkoxycarbonyl and $C_2$–$C_6$-alkanoylamino. The heteroaryl group also may be substituted with a fused ring system, e.g., a benzo or naphtho residue, which may be unsubstituted or substituted, for example, with up to three of the groups set forth in the preceding sentence.

Reference will now be made in detail to the present aspects of the invention. Wherever possible, the same reference numbers and letters are used throughout the various formulas in the invention to refer to the same or like parts.

The present invention relates to the synthesis of enantiomerically pure lactam-substituted propanoic acid derivatives and methods of making and using therefor. A reaction scheme that depicts a general sequence of reaction steps to produce the compounds of the invention is shown in Scheme 1.

SCHEME 1

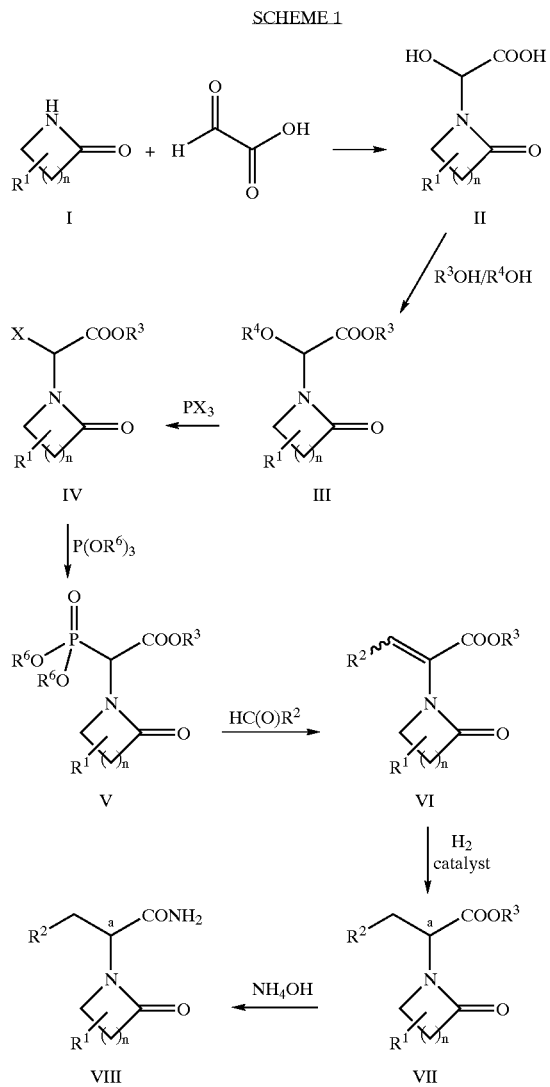

The first step depicted in Scheme 1 involves the reaction (i.e., condensation) between a compound having the formula I

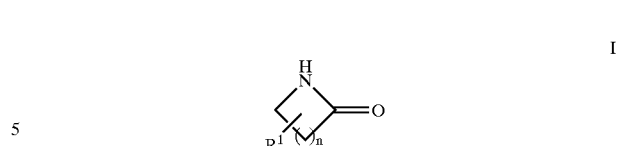

with glyoxylic acid, wherein $R^1$ is hydrogen, substituted or unsubstituted, branched or straight chain $C_1$ to $C_{20}$ alkyl; substituted or unsubstituted $C_3$ to $C_8$ cycloalkyl; substituted or unsubstituted $C_6$ to $C_{20}$ aryl; or substituted or unsubstituted $C_4$ to $C_{20}$ heteroaryl, and n is from 0 to 5, to produce a compound having the formula II.

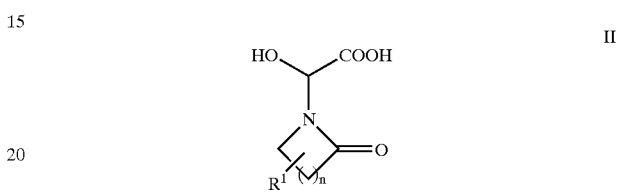

The condensation reaction between lactam I and glyoxylic acid is generally conducted in a solvent. Examples of useful solvents include, but are not limited to, aliphatic hydrocarbons such as hexane, heptane, octane and the like, aromatic hydrocarbons such as toluene, xylenes, and the like, cyclic or acyclic ethers such as diethyl ether, tert-butyl methyl ether, diisopropyl ether, tetrahydrofuran and the like, or polar aprotic solvents such as dimethylformamide, dimethyl sulfoxide, N-methylpyrrolidone and the like. The amount of glyoxylic acid relative to the amount of compound I can vary. In one aspect, the glyoxylic acid is present in the amount from 0.8 to 2 equivalents per 1.0 equivalent of the compound having the formula I. The condensation reaction is generally run between ambient temperature and the boiling point of the lowest boiling component of the mixture.

The second step depicted in Scheme 1 involves converting compound II to a compound having the formula III

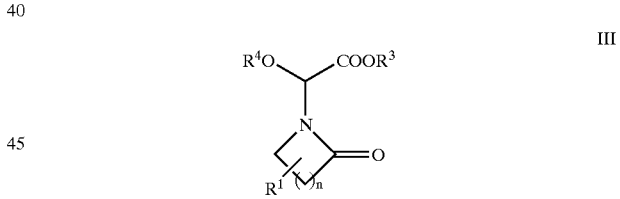

wherein $R^1$, $R^3$, and $R^4$ are, independently, a substituted or unsubstituted, branched or straight chain $C_1$ to $C_{20}$ alkyl group; a substituted or unsubstituted $C_3$ to $C_8$ cycloalkyl group; a substituted or unsubstituted $C_6$ to $C_{20}$ aryl group; or a substituted or unsubstituted $C_4$ to $C_{20}$ heteroaryl group, wherein $R^1$ can also be hydrogen, and n is from 0 to 5.

The second step generally involves reacting a compound having the formula II with an alcohol comprising an alkyl alcohol, an aryl alcohol, or a heteroaryl alcohol, wherein the alkyl alcohol is substituted or unsubstituted, branched or straight chain $C_1$ to $C_{20}$ alkyl or substituted or unsubstituted $C_3$ to $C_8$ cycloalkyl; the aryl alcohol is substituted or unsubstituted $C_6$ to $C_{20}$ aryl; and the heteroaryl alcohol is substituted or unsubstituted $C_4$ to $C_{20}$ heteroaryl, wherein the heteroatom is oxygen, nitrogen, or sulfur. Although $R^3$ and $R^4$ need not be the same group, they can be derived from the same alcohol. In one aspect, the alcohol is a $C_1$ to $C_5$ alcohol, preferably methanol or ethanol. The amount of alcohol that is used can vary. In one aspect, the alcohol is present in the amount from 2.0 to 5.0 equivalents per 1.0 equivalent of the compound having the formula II.

In another aspect, the second step is generally conducted under dehydrating conditions using acid catalysis. For example, the use of a dehydrating agent such as a trialkyl orthoformate or the physical removal of water from the reaction mixture via an azeotropic distillation are useful in the present invention. When a dehydrating agent is used, the amount of dehydrating agent used relative to the amount of compound II is generally between 2 and 5 molar equivalents. In general, the alcohol can be used as the reaction solvent for the preparation of compound III; however, co-solvents can be used. Examples of co-solvents useful in the present invention include, but are not limited to, aliphatic hydrocarbons such as hexane, heptane, octane and the like, aromatic hydrocarbons such as toluene, xylenes, and the like. A preferable co-solvent is toluene or xylene. The second step is generally performed at a temperature between ambient temperature and the boiling point of the lowest boiling component of the reaction mixture. In one aspect, the reaction is performed between 20° C. and 120° C.

The compounds produced in steps 1 and 2 can be represented by the general formula XI

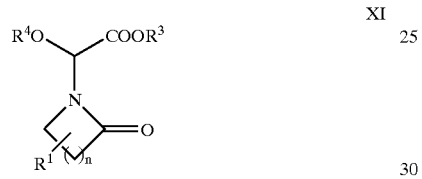

XI wherein $R^1$, $R^3$, and $R^4$ are, independently, hydrogen, a substituted or unsubstituted, branched or straight chain $C_1$ to $C_{20}$ alkyl group; a substituted or unsubstituted $C_3$ to $C_8$ cycloalkyl group; a substituted or unsubstituted $C_6$ to $C_{20}$ aryl group; or substituted or unsubstituted $C_4$ to $C_{20}$ heteroaryl group, and n is from 0 to 5. In one aspect, n is 2. In another aspect, $R^1$, $R^3$, and $R^4$ are hydrogen and n is 2. In a further aspect, $R^1$ is hydrogen, $R^3$ and $R^4$ are methyl, and n is 2.

The third step in Scheme 1 involves converting compound III to the halogenated lactam compound having the formula IV

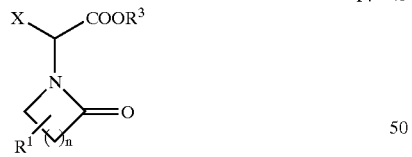

IV wherein $R^1$ and $R^3$ are, independently, substituted or unsubstituted, branched or straight chain $C_1$ to $C_{20}$ alkyl; substituted or unsubstituted $C_3$ to $C_8$ cycloalkyl; substituted or unsubstituted $C_6$ to $C_{20}$ aryl; or substituted or unsubstituted $C_4$ to $C_{20}$ heteroaryl, wherein $R^1$ can also be hydrogen, X is fluoride, chloride, bromide, or iodide, and n is from 0 to 5.

The third step generally involves reacting compound RI with a phosphorous trihalide having the formula $PX_3$, wherein X is fluoro, chloro, bromo, or iodo. In one aspect of the invention, the phosphorous trihalide is phosphorous trichloride or phosphorous tribromide. The amount of the phosphorus trihalide is generally between 0.8 and 2.0 molar equivalents based on compound III. Typically, the reaction is performed in an inert solvent including, but not limited to, aliphatic hydrocarbons such as hexane, heptane, octane and the like, aromatic hydrocarbons such as toluene, xylenes, and the like, and halogenated hydrocarbons such as dichloromethane, dichloroethane, tetrachloroethylene, chlorobenzene, and the like. The third step is generally performed at a temperature between ambient temperature and the boiling point of the lowest boiling component of the reaction mixture for a time necessary to consume the majority of compound III. In one aspect, the reaction solvent is toluene or xylene and the reaction temperature is between 40° C. and 80° C.

The fourth step in Scheme 1 involves converting compound IV to a compound having the formula V

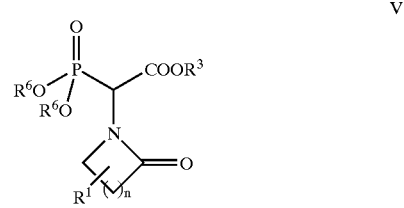

V wherein $R^1$ and $R^3$ are, independently, substituted or unsubstituted, branched or straight chain $C_1$ to $C_{20}$ alkyl; substituted or unsubstituted $C_3$ to $C_8$ cycloalkyl; substituted or unsubstituted $C_6$ to $C_{20}$ aryl; or substituted or unsubstituted $C_4$ to $C_{20}$ heteroaryl, wherein $R^1$ can also be hydrogen, $R^6$ is substituted or unsubstituted, branched or straight chain $C_1$ to $C_{20}$ alkyl or substituted or unsubstituted $C_3$ to $C_8$ cycloalkyl, and n is from 0 to 5. In one aspect, n is 2 and $R^1$ is hydrogen. In another aspect of the invention, $R^3$ is methyl or ethyl. In a further aspect, $R^6$ is methyl or ethyl.

The fourth step is an Arbuzov reaction comprising reacting a compound having the formula IV with a phosphite having the formula $P(OR^6)_3$, wherein $R^6$ is substituted or unsubstituted, branched or straight chain $C_1$ to $C_{20}$ alkyl or substituted or unsubstituted $C_3$ to $C_8$ cycloalkyl. In one aspect, the phosphite is trimethyl phosphite or triethyl phosphite. In another aspect of the invention, compound IV is the chloro or bromo compound (X=Cl or Br). The amount of the phosphite is generally between 0.8 and 1.2 molar equivalents based on compound IV. The reaction is optionally conducted in the presence of a solvent including, but not limited to, aliphatic hydrocarbons such as hexane, heptane, octane and the like, aromatic hydrocarbons such as toluene, xylenes, and the like, cyclic or acyclic ethers such as tert-butyl methyl ether, diisopropyl ether, tetrahydrofuran and the like, halogenated hydrocarbons such as dichloromethane, dichloroethane, tetrachloroethylene, chlorobenzene and the like, or polar aprotic solvents such as dimethylformamide, dimethyl sulfoxide, N-methylpyrrolidone and the like. The reaction is generally performed at a temperature between ambient temperature and the boiling point of the lowest boiling component of the reaction mixture for a time necessary to consume the majority of compound IV. In one aspect, the solvent is toluene or xylene and the reaction is performed between 40° C. and 100° C.

The fifth step in Scheme 1 involves converting compound V to a compound having the formula VI

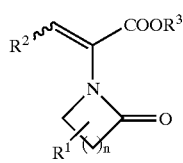

VI wherein $R^1$, $R^2$, and $R^3$ are, independently, hydrogen, substituted or unsubstituted, branched or straight chain $C_1$ to $C_{20}$ alkyl; substituted or unsubstituted $C_3$ to $C_8$ cycloalkyl; substituted or unsubstituted $C_6$ to $C_{20}$ aryl; or substituted or unsubstituted $C_4$ to $C_{20}$ heteroaryl, and n is from 0 to 5. In one aspect, n is 2 and $R^1$ is hydrogen. In another aspect, $R^2$ and $R^3$ are methyl. In a further aspect, $R^2$ is methyl and $R^3$ is ethyl.

The fifth step of the sequence is a Horner-Emmons Wittig reaction between phosphonate compound V and an aldehyde having the formula $HC(O)R^2$ to afford enamide VI. In one aspect of the invention, the aldehyde is acetaldehyde. The reaction generally involves the use of a base. For example, the base can be a moderately strong non-hydroxide base with a pKa of about 13 or above. Examples of non-hydroxide bases include, but are not limited to, amidine bases such as 1,5-diazabicyclo[4.3.0]non-5-ene (DBN), 1,8-diazabicyclo[5.4.0]undec-7-ene (DBU), or guanidine bases such as tetramethylguanidine (TMG). The amount of base is usually between 1.0 and 2.0 molar equivalents based on compound V, and the amount of aldehyde is generally between 0.8 and 1.5 molar equivalents based compound V.

The reaction to produce compound VI is generally conducted in the presence of a solvent. Solvents useful in the reaction include, but are not limited to, aliphatic hydrocarbons such as hexane, heptane, octane and the like, aromatic hydrocarbons such as toluene, xylenes, and the like, cyclic or acyclic ethers such as tert-butyl methyl ether, diisopropyl ether, tetrahydrofuran and the like, halogenated hydrocarbons such as dichloromethane, dichloroethane, tetrachloroethylene, chlorobenzene and the like, or polar aprotic solvents such as dimethylformamide, dimethyl sulfoxide, N-methylpyrrolidone and the like. The reaction is generally performed at a temperature between −80° C. and the boiling point of the lowest boiling component of the reaction mixture for a time necessary to largely consume compound V. In one aspect of the invention, the reaction is performed in toluene or xylene at a temperature of 0° C. to 50° C.

The invention also contemplates producing compound VI from compound III in situ. The term "in situ" is defined herein as performing two or more reaction sequences without isolating any of the intermediates that are produced during the reaction sequence. One aspect of the invention involves a method for producing the compound VI in situ, comprising (a) reacting a compound having the formula III

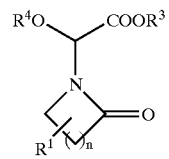

III wherein $R^3$ and $R^4$ are a substituted or unsubstituted, branched or straight chain $C_1$ to $C_{20}$ alkyl group; a substituted or unsubstituted $C_3$ to $C_8$ cycloalkyl group; a substituted or unsubstituted $C_6$ to $C_{20}$ aryl group; or substituted or unsubstituted $C_4$ to $C_{20}$ heteroaryl group, wherein $R^1$ can also be hydrogen,
with $PX_3$, wherein X is fluoride, chloride, bromide, or iodide, to produce a halogenated lactam;
(b) reacting the halogenated lactam produced in step (a) with a phosphite having the formula $P(OR^6)_3$, wherein $R^6$ is substituted or unsubstituted, branched or straight chain $C_1$ to $C_{20}$ alkyl or substituted or unsubstituted $C_3$ to $C_8$ cycloalkyl, to produce a phosphonated lactam; and
(c) reacting the phosphonated lactam produced in step (b) with an aldehyde having the formula $HC(O)R^2$, wherein $R^2$ is hydrogen, substituted or unsubstituted, branched or straight chain $C_1$ to $C_{20}$ alkyl; substituted or unsubstituted $C_3$ to $C_8$ cycloalkyl; substituted or unsubstituted $C_6$ to $C_{20}$ aryl; or substituted or unsubstituted $C_4$ to $C_{20}$ heteroaryl, in the presence of a base,
wherein steps (a), (b), and (c) are performed in situ. In this aspect of the invention, compounds IV and V are not isolated. The in situ preparation of compound VI would not have been expected due to the incompatibility of several of the reagents used in the in situ process. In addition, there is an economic advantage to combining multiple reaction steps without having to isolate each of compound that is produced.

The sixth step in Scheme 1 involves converting compound VI to a compound having the formula VII

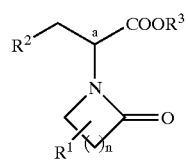

VII wherein $R^1$, $R^2$, and $R^3$ are, independently, hydrogen, a substituted or unsubstituted, branched or straight chain $C_1$ to $C_{20}$ alkyl group; a substituted or unsubstituted $C_3$ to $C_8$ cycloalkyl group; a substituted or unsubstituted $C_6$ to $C_{20}$ aryl group; or substituted or unsubstituted $C_4$ to $C_{20}$ heteroaryl group,
n is from 0 to 5, and
the stereochemistry at carbon a is substantially R or S.

The term "substantially R or S" refers to the enantiomeric purity of the aformentioned compound, which is measured by the enantiomeric excess of this material. The enantiomeric excess (ee) is defined as the percent of one enantiomer of the mixture minus the percent of the other enantiomer. "Substantially R" indicates an ee of 90% or greater with the R enantiomer the major enantiomer, whilst "substantially S" indicates an ee of 90% or greater with the S enantiomer the major enantiomer. In one aspect of the invention, the stereochemistry at carbon a is substantially S. In another aspect of the invention, the stereochemistry at carbon a is substantially R.

In other aspects of the invention, the heteroatom of the heteroaryl group in compound VII is oxygen, sulfur, or nitrogen, and the substituent on the substituted alkyl, aryl, or heteroaryl group comprises alkyl, aryl, hydroxy, alkoxy, fluoro, chloro, bromo, iodo, nitro, cyano, or an ester; $R^2$ and $R^3$ are independently selected from methyl or ethyl; $R^1$ is hydrogen, $R^2$ is methyl, $R_3$ is methyl or ethyl; and n is 2.

The conversion of compound VI to compound VII comprises hydrogenating compound VI with hydrogen in the presence of a catalyst comprised of a chiral ligand/metal complex to asymmetrically hydrogenate the carbon-carbon double bond of compound VI. The term "hydrogenate" generally refers to reacting a carbon-carbon double or triple bond with hydrogen to reduce the degree of unsaturation. For example, the carbon-carbon double bond of compound VI is hydrogenated to produce a carbon-carbon single bond. Here, the degree of unstauration has been reduced by one. Referring to Scheme 2, hydrogen can be added to side b (front side) or c (back side) of the carbon-carbon double bond of compound VII. The stereochemistry at carbon a of compound VII will be determined by which side of the carbon-carbon double bond hydrogen approaches. The term "asymmetrically hydrogenating" refers to the addition of hydrogen to a particular side or face (b or c) of the carbon-carbon double bond of compound VII in preference to the other side. The degree of asymmetric hydrogenation is described by the enantiomeric excess of the asymmetric hydrogenation product.

SCHEME 2

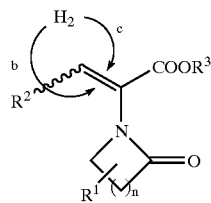

VI

The asymmetric hydrogenation of compound VI involves the use of a chiral ligand/metal complex. The chiral ligand/metal complex is composed of a chiral ligand and a metal, where the metal is either chemically bonded to the chiral ligand or the metal is coordinated to the chiral ligand. Any chiral ligand/metal complex known in the art can be used to asymmetrically hydrogenate compound VI. For example, the chiral ligand/metal complexes disclosed in Ohkuma et al. in *Catalytic Asymmetric Synthesis*, 2$^{nd}$ Ed, Wiley-VCH, 2000, pages 1–17, which is incorporated by reference in its entirety, are useful in the present invention.

In one aspect of the invention, the chiral ligand of the chiral ligand/metal complex comprises the substantially pure enantiomer or diastereomer of 2,3-O-isopropylidene-2,3-dihydroxy-1,4-bis(diphenylphosphino)butane; 2,2'-bis (diphenylphosphino)-1,1'-binaphthyl; 1,2-bis-2,5-dialkylphospholano(benzene); 1,2-bis-2,5-dialkylphospholano(ethane); 2,3-bis-(diphenylphosphino) butane; or 2-diphenylphosphinomethyl-4-diphenylphophino-1-t-butoxycarbonylpyrrolidine.

In another aspect of the invention, the chiral ligand of the chiral ligand/metal complex comprises a substantially enantiomerically pure bis-phosphine compound comprising one phosphine residue having three phosphorus-carbon bonds and the other having two phosphorus-carbon bonds and one phosphorus-nitrogen bond. In one aspect of the invention, the chiral ligand of the chiral ligand/metal complex comprises a phosphine or a bis-phosphine compound and the metal of the chiral ligand/metal complex comprises rhodium, ruthenium, or iridium.

Examples of substantially enantiomerically pure bis-phosphine compounds, e.g., an enantiomeric excess of 90% or greater, include phosphinometallocenyl-aminophosphines having the general formulas IX and X (the enantiomer of IX):

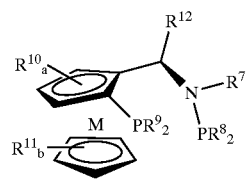

IX

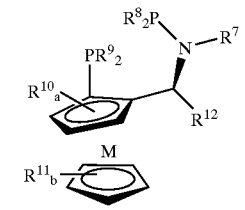

X where $R^7$, $R^8$, $R^9$, $R^{10}$, $R^{11}$, and $R^{12}$ are, independently, hydrogen, substituted or unsubstituted branched or straight chain $C_1$ to $C_{20}$ alkyl, substituted or unsubstituted $C_3$ to $C_8$ cycloalkyl, substituted or unsubstituted $C_6$ to $C_{20}$ aryl, and substituted or unsubstituted $C_4$ to $C_{20}$ heteroaryl, where the heteroatoms are chosen from sulfur, nitrogen, or oxygen, provided $R^{12}$ is not hydrogen;

a is from 0 and 3;

b is from 0 and 5; and

M is a Group IV to Group VIII metal. The synthesis of the chiral ligands having the formulas IX and X is disclosed in U.S. Provisional Application Nos. 60/236,564 and 60/264,411, both of which are incorporated by reference in their entireties.

The alkyl groups that may be represented by each of $R^7$, $R^8$, $R^9$, $R^{10}$, $R^{11}$, and $R^{12}$ in formulas IX and X may be straight- or branched-chain, aliphatic hydrocarbon radicals containing up to about 20 carbon atoms and may be substituted, for example, with one to three groups selected from $C_1$–$C_6$-alkoxy, cyano, $C_2$–$C_6$-alkoxycarbonyl, $C_2$–$C_6$ alkanoyloxy, hydroxy, aryl and halogen. The terms "$C_1$–$C_6$-alkoxy," "$C_2$–$C_6$-alkoxycarbonyl," and "$C_2$–$C_6$-alkanoyloxy" are used to denote radicals corresponding to the structures —$OR^{13}$, —$CO_2R^{13}$, and —$OCOR^{13}$, respectively, wherein $R^{13}$ is $C_1$–$C_6$-alkyl or substituted $C_1$–$C_6$-alkyl. The term "$C_3$–$C_8$-cycloalkyl" is used to denote a saturated, carbocyclic hydrocarbon radical having three to eight carbon atoms.

The aryl groups for each of $R^7$, $R^8$, $R^9$, $R^{10}$, $R^{11}$, and $R^{12}$ in formulas IX and X may include phenyl, naphthyl, or anthracenyl and phenyl, naphthyl, or anthracenyl substituted with one to three substituents selected from $C_1$–$C_6$-alkyl, substituted $C_1$–$C_6$-alkyl, $C_6$–$C_{10}$ aryl, substituted $C_6$–$C_{10}$ aryl, $C_1$–$C_6$-alkoxy, halogen, carboxy, cyano, $C_1$–$C_6$-alkanoyloxy, $C_1$–$C_6$-alkylthio, $C_1$–$C_6$-alkylsulfonyl, trifluoromethyl, hydroxy, $C_2$–$C_6$-alkoxycarbonyl, $C_2$–$C_6$-alkanoylamino and —O—$R^{14}$, S—$R^{14}$, —$SO_2$—$R^{14}$, —$NHSO_2R^{14}$ and —$NHCO_2R^{14}$, wherein $R^{14}$ is phenyl, naphthyl, or phenyl or naphthly substituted with one to three groups selected from $C_1$–$C_6$-alkyl, $C_6$–$C_{10}$ aryl, $C_1$–$C_6$-alkoxy and halogen.

The heteroaryl radicals include a 5- or 6-membered aromatic ring containing one to three heteroatoms selected from oxygen, sulfur and nitrogen. Examples of such heteroaryl groups are thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridyl, pyrimidyl, benzoxazolyl, benzothiazolyl, benzimidazolyl, indolyl and the like. The heteroaryl radicals may be substituted, for example, with up to three groups such as $C_1$–$C_6$-alkyl, $C_1$–$C_6$-alkoxy, substituted $C_1$–$C_6$-alkyl, halogen, $C_1$–$C_6$-alkylthio, aryl, arylthio, aryloxy, $C_2$–$C_6$-alkoxycarbonyl and $C_2$–$C_6$-alkanoylamino. The heteroaryl radicals also may be substituted with a fused ring system, e.g., a benzo or naphtho residue, which may be unsubstituted or substituted, for example, with up to three of the groups set forth in the preceding sentence. The term "halogen" is used to include fluorine, chlorine, bromine, and iodine.

In one aspect of the invention, when the chiral ligand is a compound having the formula IX or X, $R^{12}$ is $C_1$ to $C_6$ alkyl (e.g., methyl); $R^7$ is hydrogen or $C_1$ to $C_6$ alkyl (e.g., methyl); $R^8$ is aryl (e.g., phenyl), ethyl, isopropyl, or cyclohexyl; $R^9$ is aryl (e.g., phenyl); $R^{10}$ and $R^{11}$ are hydrogen; and M is iron, ruthenium, or osmium.

The chiral ligand/metal complex can be prepared and isolated, or, in the alternative, it can be prepared in situ. The preparation of chiral ligand/metal complexes is generally known in the art. The chiral ligand to metal molar ratio can be from 0.5:1 to 5:1, preferably from 1:1 to 1.5:1. The amount of chiral ligand/metal complex may vary between 0.0005 and 0.5 equivalents based on compound VI, with more catalyst leading to a faster reaction.

The hydrogenation reaction is conducted under an atmosphere of hydrogen, but other materials that are inert to the reaction conditions may also be present. The reaction can be run at atmospheric pressure or at elevated pressure of from 0.5 to 200 atmospheres. The reaction temperature can be varied to modify the rate of conversion, usually between ambient temperature and the boiling point (or apparent boiling point at elevated pressure) of the lowest boiling component of the reaction mixture. In one aspect of the invention, the hydrogenation step is conducted at from –20° C. to 100° C. The reaction is usually run in the presence of a solvent. Examples of useful solvents include, but are not limited to, aliphatic hydrocarbons such as hexane, heptane, octane and the like, aromatic hydrocarbons such as toluene, xylenes, and the like, cyclic or acyclic ethers such as tert-butyl methyl ether, diisopropyl ether, tetrahydrofuran and the like, dialkyl ketones such as acetone, diethyl ketone, methyl ethyl ketone, methyl propyl ketone and the like, or polar aprotic solvents such as dimethylformamide, dimethyl sulfoxide, N-methylpyrrolidone and the like.

Compounds having the formula VII can be converted to the amide compounds VIII

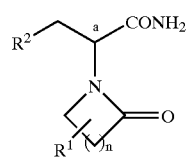

VIII wherein $R^1$ and $R^2$ are, independently, hydrogen, substituted or unsubstituted, branched or straight chain $C_1$ to $C_{20}$ alkyl; substituted or unsubstituted $C_3$ to $C_8$ cycloalkyl; substituted or unsubstituted $C_6$ to $C_{20}$ aryl; or substituted or unsubstituted $C_4$ to $C_{20}$ heteroaryl,
n is from 0 to 5, and the stereochemistry at carbon a is substantially R or S, comprising reacting a compound having the formula VII with $NH_4OH$.

The amount of $NH_4OH$ can vary, wherein from 1 to 10 equivalents of $NH_4OH$ per 1.0 equivalent of the compound having the formula VII can be used. The reaction is generally performed in water optionally in the presence of a water-miscible organic solvent, including, but not limited to, a lower alcohol such as methanol or ethanol, THF, DMF, or DMSO. The reaction is preferably performed in water as the sole solvent. The reaction temperature can also vary, however; the reaction is typically performed from 0° C. to 50° C. The compounds having the formula VIII can be used to treat a number of different maladies, some of which are disclosed in U.S. Pat. No. 4,696,943, which is incorporated by reference in its entirety.

In summary, the invention provides lactam-substituted propanoic acid derivatives that are useful precursors to enantiomerically-pure lactam-substituted propanoic acid derivatives. The invention provides an efficient method for making the lactam-substituted propanoic acid derivatives as well as the enantiomerically enriched compounds, which will ultimately be used to produce pharmaceutical compounds.

Throughout this application, where publications are referenced, the disclosures of these publications in their entireties are hereby incorporated by reference into this application in order to more fully describe the state of the art to which this invention pertains.

EXAMPLES

The following examples are put forth so as to provide those of ordinary skill in the art with a complete disclosure and description of how the compositions of matter and methods claimed herein are made and evaluated, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are by weight, temperature is in ° C. or is at room temperature and pressure is at or near atmospheric.

Example 1

Preparation of Methyl 2-(2-Pyrrolidino)Propanoate

Step 1: Preparation of Hydroxy-Acid 2a (Formula II, n=2, $R^1$=$R^3$=$R^4$=H):

Glyoxylic acid monohydrate (20.2 g; 220 mmol; 1.1 equiv) was slurried in 200 mL of diethyl ether. Pyrrolidinone (15.2 mL; 200 mmol) was added and the resulting mixture was stirred at ambient temperature for two days to afford a white precipitate. The precipitate was isolated by filtration, washed with ether, and air-dried to afford 36.06 g (99%) of hydroxy-acid 2a.

$^1$H NMR (DMSO-$d_6$) δ 5.55 (s, 1 H); 3.5–3.3 (m, 2H); 3.36 (s, 3H); 2.46 (m, 2H); 2.07 (m, 2H).

Step 2: Preparation of Ether-Ester 3a (Formula III n=2, $R^1$=H, $R^3$=$R^4$=Me):

Hydroxy-acid 2a (25.3 g; 160 mmol) was dissolved in methanol (370 mL), cooled in ice-water, and treated with concentrated sulfuric acid (5.0 mL; 0.093 mmol; 0.57 molar equiv). The reaction mixture was allowed to warm to ambient temperature and allowed to stir for 5 days. Solid sodium bicarbonate (17.1 g; 203 mmol; 1.27 equiv) was added and the reaction mixture was stirred for 30 min. The reaction mixture was filtered and the filtrate was concentrated. The resulting material was diluted with water (25 mL) and extracted with ethyl acetate (2×50 mL). The combined extracts were dried with magnesium sulfate and the solvent was evaporated to afford 22.84 g (76%) of 3a.

$^1$H NMR (CDCl$_3$) δ 5.64 (s, 1 H); 3.78 (s, 3H); 3.40 (m, 1H); 3.16 (m, 1H); 2.24 (m, 2H); 1.90 (m, 2H).

Steps 3 and 4: Preparation of Phosphonate Ester 5a (Formula V, n=2, R$^1$=H, R$^3$=R$^6$=Me):

Ether-ester 3a (9.36 g; 50 mmol) was dissolved in 50 mL of toluene. The reaction mixture was heated to 70° C. and phosphorus trichloride (4.36 mL; 50 mmol; 1.0 equiv) was added. The reaction mixture was heated at 70° C. for 18 h to afford chloride 4a (formula IV, X=Cl, R$^3$=Me). Trimethyl phosphite (5.9 mL; 50 mmol; 1.0 equiv) was then added. The resulting mixture was heated for 36 h and then cooled to ambient temperature. The volatiles were stripped at reduced pressure and the remaining material was dissolved in 100 mL of ethyl acetate. The mixture was washed with saturated aqueous sodium bicarbonate (2×25 mL), and the resulting aqueous solution was back-extracted three times with ethyl acetate. The combined ethyl acetate solution was dried with magnesium sulfate and concentrated to afford 4.35 g (33%) of phosphonate 5a.

$^1$H NMR (CDCl$_3$) δ 5.46 (d, 1H, J$_{P-H}$=24.72 Hz); 3.84 (d, 3H, J$_{P-H}$=10.99 Hz); 3.80 (s, 3H); 3.78 (d, 3H, J$_{P-H}$=11.26 Hz) 3.8 (m, 1H); 3.66 (m, 1H); 2.42 (m, 2H); 2.08 (m, 2 H).

Step 5: Preparation of Enamide 6a (Formula VI, n=2, R$^1$=H, R$^2$=R$^3$=Me):

Phosphonate 5a (2.65 g; 10 mmol) was dissolved in 10 mL of tetrahydrofuran. The mixture was cooled to −78° C. and tetramethylguanidine (2.88 mL; 15 mmol; 1.5 equiv) was added. The reaction mixture was stirred for 15 min and acetaldehyde (0.84 mL; 15 mmol; 1.5 equiv) was added. The resulting mixture was stirred at −78° C. for 1 h and then warmed to ambient temperature and stirred overnight. The volatiles were evaporated at reduced pressure and water (10 mL) was added. The mixture was extracted three times with ethyl acetate and the combined extracts were dried with magnesium sulfate and concentrated. The crude product was filtered through a pad of flash silica gel and eluted with ethyl acetate to afford 1.37 g (75%) of 6a as a mixture of E and Z isomers.

E-6a: $^1$H NMR (CDCl$_3$) δ 7.05 (q, 1H, J=7.14 Hz); 3.74 (s, 3H); 3.55 (t, 2H, J=6.86 Hz); 2.46 (m, 2H); 2.15 (m, 2H); 1.77 (d, 3H, J=7.19 Hz).

Z-6a: 1H NMR (CDCl$_3$) δ 5.99 (q, 1H, J=7.42 Hz); 3.78 (s, 3H); 2.02 (d, 3H, J=7.42 Hz).

Step 6: Hydrogenation of Enamide 6a to Afford Ester 7a (Formula VII, n=2, R$^1$=H, R$^2$=R$^3$=Me) Using Ligand 9a (Formula IX, R$^{12}$=R$^7$=Me, R$^8$=R$^9$=Ph, a=b=0, M=Fe):

A Fischer-Porter tube was charged with ligand 9a (22 mg, 0.036 mmol; 0.064 equiv) and anhydrous THF (4.0 mL) under an argon atmosphere. Argon was bubbled through the solution for 20 minutes before the addition of bis(1,5-cyclooctadienyl)rhodium trifluoromethanesulfonate (12 mg; 0.026 mmol; 0.047 equiv). The solution was stirred at 25° C. for 5 minutes or until all bis(1,5-cyclooctadienyl)rhodium trifluoromethanesulfonate had dissolved. Enamide 5a (100 mg, 0.55 mmol) was added via syringe. The vessel was capped and pressurized to 40 psi H$_2$. After 18 hours, the mixture was diluted with hexane (4.0 mL) and filtered through silica gel to remove the catalyst. The product 7a was isolated as an oil (99% yield, 96.2% ee as determined by chiral GC).

$^1$H NMR (CDCl$_3$ δ 4.71–4.65 (m, 1H), 3.71 (s, 3H), 3.55–3.47 (m, 1H), 3.38–3.30 (m, 1H), 2.45–2.40 (t, J=8.4 Hz, 2H), 2.12–1.97 (m, 3H), 1.74–1.64 (m 1H), 0.94–0.89 (t, J=7.5 Hz, 3H). Chiral GC analysis [Cyclosil-B (J&W Scientific), 40° C. for 4 min to 175° C. at 70° C./min, hold at 175° C. for 12 minutes: t$_R$=23.19 (major enantiomer), t$_R$=23.24 (minor enantiomer)].

Example 2

In Situ Preparation of Compound VI (n=2, R$^1$=H, R$^2$=R$^3$=Me):

Ether-ester 3a (9.36 g; 50 mmol) was dissolved in 25 mL of toluene. The reaction mixture was heated to 50° C. and phosphorus trichloride (4.4 mL; 50 mmol; 1.0 equiv) was added and the mixture was held at 50° C. for 16 h. The reaction mixture was cooled to ambient temperature and sodium bicarbonate (10.5 g; 125 mmol; 2.5 equiv) was added. The mixture was stirred for 15 min, filtered, and the volatiles were stripped. The solution was reconstituted by the addition of toluene (25 mL) and heated to 70° C. Trimethyl phosphite (6.5 mL; 55 mmol; 1.1 equiv) was added and the reaction mixture was heated at 70° C. for 24 h to completely consume 4a. The mixture was then cooled to 2° C. and acetaldehyde (4.2 mL; 75 mmol; 1.5 equiv) was added. Tetramethylguanidine (9.41 mL; 75 mmol; 1.5 equiv) was then added slowly dropwise with an attendant exotherm to 8.5° C. The reaction mixture was allowed to warm to ambient temperature and stirred overnight to consume phosphonate 5a. Water (15 mL) was added and the layers were separated. The aqueous layer was extracted with ethyl acetate (2×15 mL) and the organic solutions were dried and concentrated to afford a total of 9.23 g of crude 6a. This material was filtered through a pad of flash silica gel and eluted with ethyl acetate to afford 7.13 g (78% overall from 3a) of 6a.

Example 3

Preparation of Ethyl 2-(2-Pyrrolidino)Propanoate

Step, 2: Preparation of Ether-Ester 3b (Formula III, n=2, R$^1$=H, R$^3$=R$^4$=Et):

Hydroxy-acid 2a (7.96 g; 50 mmol) was dissolved in ethanol (25 mL), and triethyl orthoformate (18.3 mL; 110 mmol; 2.2 equiv) was added. p-Toluenesulfonic acid (0.48 g; 2.5 mmol; 0.05 equiv) was added and the reaction mixture was heated to 60° C. for 24 h. Solid sodium bicarbonate (0.50 g; 6 mmol; 0.12 equiv) was added and the reaction mixture was stirred for 15 min. The volatiles were evaporated at reduced pressure and the remaining material was dissolved in 1:1 toluene:ethyl acetate (25 mL), filtered, and concentrated to afford 10.25 g (95%) of 3b.

$^1$H NMR (CDCl$_3$) δ 5.72 (s, 1H); 4.24 (q, 2H, J=7.14 Hz); 3.57 (q, 2H, J=6.87 Hz); 3.5–3.3 (m, 2H); 2.47 (t, 2H, J=7.42 Hz); 2.06 (m(5), 2H, J=7.42 Hz); 1.29 (t, 3H, J=7.14 Hz); 1.25 (t, 3H, J=6.87 Hz).

Steps 3 and 4: Preparation of Phosphonate Ester 5b (Formula V, n=2, R$^1$=H, R$^3$=Et R$^6$=Me):

Ether-ester 3b (5.38 g; 25 mmol) was dissolved in 12.5 mL of toluene. The reaction mixture was heated to 50° C. and phosphorus trichloride (2.2 mL; 25 mmol; 1.0 equiv) was added. The reaction mixture was heated at 50° C. for 12 h and then at 70° C. for 24 h to completely consume 3b and afford chloride 4b (formula IV, X=Cl, R$^3$=Et). Solid sodium bicarbonate (5.25 g; 62.5 mmol; 2.5 equiv) was added and the mixture was stirred for 15 min. The reaction mixture was then filtered and concentrated at reduced pressure. Toluene (12.5 mL) was added and the reaction mixture was heated to 70° C. where trimethyl phosphite (3.24 mL; 25 mmol; 1.0 equiv) was added. The resulting mixture was heated at 70° C. for 24 h and then cooled to ambient temperature. The volatiles were evaporated at reduced pressure to afford 7.00 g (99%) of phosphonate 5b, which was used without further purification.

$^1$H NMR (CDCl$_3$) δ 5.43 (d, 1H, J$_{P-H}$=24.72 Hz); 4.25 (q, 2H, J=7.14 Hz); 3.84 (d, 3H, J$_{P-H}$=10.99 Hz); 3.77 (d, 3H, J$_{P-H}$=10.99 Hz) 3.8 (m, 1H); 3.66 (m, 1H); 2.40 (m, 2H); 2.06 (m, 2H); 1.29 (t, 3H, J=7.14 Hz).

Step 5: Preparation of Enamide 6b (Formula VI, n=2, R$^1$=H, R$^3$=Et, R$^2$=Me):

Phosphonate 5b (7.00 g; 25 mmol) was dissolved in 12.5 mL of toluene. The mixture was cooled to 2° C. and acetaldehyde (2.1 mL; 37.5 mmol; 1.5 equiv) was added. Tetramethylguanidine (3.5 mL; 27.5 mmol; 1.1 equiv) was added dropwise accompanied by a moderate exotherm. The reaction mixture was allowed to warm to ambient temperature and stirred overnight and then heated to 50° C. for 12 h to completely consume 5b. The reaction mixture was diluted with 3 N HCl (10 mL) and the layers were separated. The aqueous layer was extracted twice with ethyl acetate and the combined organic solution was dried with magnesium sulfate and concentrated. The crude product was filtered through a pad of flash silica gel and eluted with ethyl acetate to afford 2.85 g (58%) of 6b as a mixture of E and Z isomers.

E-6b: $^1$H NMR (CDCl$_3$) δ 7.05 (q, 1H, J=7.14 Hz); 4.20 (q, 2H, J=7.14 Hz); 3.55 (t, 2H, J=7.14 Hz); 2.48 (t, 2H, J=7.69 Hz); 2.15 (m(5), 2H, J=7.69 Hz); 1.77 (d, 3H, J=7.14 Hz); 1.28 (t, 3H, J=7.14 Hz).

Z-6b: $^1$H NMR (CDCl$_3$) δ 6.0 (q, 1H); 3.78 (s, 3H); 4.12 (q, 2H); 1.95 (d, 3H).

Step 6: Hydrogenation of Enamide 6b to Afford Ester 7b (Formula VII, n=1, R$^1$=H, R$^3$=Et, R=Me) Using Ligand 10a (X, R$^{12}$=R$^7$=Me, R$^8$=R$^9$=Ph, a=b=0, M=Fe):

Bis(1,5-cyclooctadienyl)rhodium trifluoromethanesulfonate (5 μmol, 2.3 mg) was placed into a reaction vessel and purged with argon for 20 min. A solution of 10a (6 μmol, 3.7 mg) in anhydrous THF (2.0 mL) was degassed with Ar for 20 minutes, then added via cannula to the bis(1,5-cyclooctadienyl)rhodium trifluoromethanesulfonate. This solution was stirred at 25° C. under Ar for 20 minutes. A solution of enamide 6b (0.5 mmol) in anhydrous THF (2.0 mL) was degassed with Ar for 20 minutes, then added to the catalyst solution via cannula. The solution was then flushed with H$_2$ and pressurized to 20 psig H$_2$. A sample was taken after 1 hour and analyzed for enantiomeric excess using standard chiral gas chromatography. 7b was formed in 95.0% ee with >99% conversion. Chiral GC analysis [Cyclosil-B (J&W Scientific), 30 m×0.25 mm ID, film thickness 0.25 μm, 60–140° C. 40° C./min, 140° C. 30 min, 20 psig He: t$_R$(minor enantiomer) 26.26 min, t$_R$(major enantiomer) 26.82 min.

Example 4

Preparation of Amide

Step 1: Conversion of Ester 7a (Formula VII, n=1, R$^1$=H, R$^2$=R$^3$=Me) to Amide 8 (Formula VIII, n=1, R$^1$=H, R$^2$=Me):

Ester 7a (93.6% ee; 0.93 g; 5.0 mmol) was combined with ammonium hydroxide (28% NH$_3$; 1.0 mL; 15 mmol; 3 equiv) and stirred at ambient temperature overnight, at which time tlc analysis indicated no 7a. The mixture was diluted with water (5 mL) and extracted with three 5 mL portions of dichloromethane. The combined extracts were dried with sodium sulfate and concentrated to afford 0.62 g (73%) of 8 which possessed 92.6% ee according to chiral GC analysis, indicating very little loss of enantiomeric purity. The crude product was recrystallized from hot acetone (3.1 mL; 5 mL/g) by cooling to 0° C. The resulting crystals were collected by filtration, washed with 1:1 acetone:heptane, and air-dried to afford 0.37 g (43%) of 8 which was 99.6% ee according to chiral GC.

$^1$H NMR (CDCl$_3$ δ 6.43 (br s, 1H); 5.72 (br s, 1H); 4.455 (dd, 11H, J=9.07, 6.87 Hz); 3.38 (m, 2H); 2.40 (m, 2H); 2.1–1.9 (m, 3H); 1.67 (m, 1H); 0.886 (t, 3H, J=7.42 Hz). Chiral GC analysis [Cyclosil-B (J&W Scientific), 175° C. for 25 minutes, 15 psi He]: t$_R$=21.31 (S enantiomer), t$_R$=22.06 (R enantiomer)]. [α]$_D^{22}$ −86.7° (c 0.98, acetone).

Comparative Example

Conversion of Ester 7a (Formula VII, n=1, R$^1$=H R$^2$=R$^3$=Me) to Amide 8 (Formula VIII, n=1, R$^1$=H, R$^2$=Me):

Ester 7a (93.6% ee; 0.93 g; 5.0 mmol) was dissolved in 2 mL of methanol and treated with ammonium hydroxide (28% ammonia; 1.0 mL; 15 mmol; 3 equiv). The mixture was stirred at ambient temperature overnight, at which time tlc analysis indicated some residual 7a. Additional ammonium hydroxide (1.0 mL; 15 mmol; 3 equiv) was added and the reaction mixture was stirred for 2 days to completely consume 7a. The reaction mixture was evaporated under reduced pressure and azeotroped several times with toluene under reduced pressure to afford 0.95 g of 8 as a brown oil which was 89.4% ee according to chiral GC analysis, indicating substantial loss of enantiomeric purity.

The invention has been described in detail with particular reference to specific aspects thereof, but it will be understood that variations and modifications can be effected without departing from the scope and spirit of the invention.

What is claimed is:

1. A method for producing a compound having the formula VI

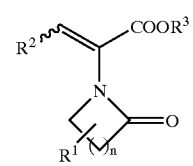

VI comprising (a) reacting a compound having the formula III

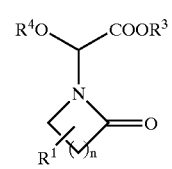

III with PX$_3$, wherein X is fluoride, chloride, bromide, or iodide, to produce a halogenated lactam;

(b) reacting the halogenated lactam produced in step (a) with a phosphite having the formula P(OR$^8$)$_3$, wherein R$^6$ is branched or straight chain C$_1$ to C$_{20}$ alkyl, branched or straight chain C$_1$ to C$_{20}$ alkyl substituted with one to three groups selected from cyano, hydroxy, aryl, halogen, —OR, —CO$_2$R, and —OCOR, C$_3$ to C$_8$ cycloalkyl, or C$_3$ to C$_8$ cycloalkyl substituted with one to three groups selected from cyano, hydroxy, aryl, halogen, —OR, —CO$_2$R, and —OCOR, to produce a phosphonated lactam; and (c) reacting the phosphonated lactam produced in step (b) with an aldehyde having the formula HC(O)R$^2$ in the presence of a base, wherein steps (a), (b), and (c) are performed in situ, and wherein $R^1$, $R^2$, $R^3$ and $R^4$ are, independently, branched or straight chain $C_1$ to $C_{20}$ alkyl; branched or straight chain $C_1$ to $C_{20}$ alkyl substituted with one to three groups selected from cyano, hydroxy, aryl, halogen, —OR, —$CO_2R$, and —OCOR; $C_3$ to $C_8$ cycloalkyl; $C_3$ to $C_8$ cycloalkyl substituted with one to three groups selected from cyano, hydroxy, aryl, halogen, —OR, —$CO_2R$, and —OCOR; $C_6$ to $C_{20}$ aryl; $C_6$ to $C_{20}$ aryl substituted with one to three groups selected from $C_1$–$C_6$-alkyl, $C_6$–$C_{10}$ aryl, $C_1$–$C_6$-alkoxy, halogen, carboxy, cyano, $C_1$–$C_6$-alkanoyloxy, $C_1$–$C_6$-alkylthio, $C_1$–$C_6$-alkylsulfonyl, trifluoromethyl, hydroxy, $C_2$–$C_6$-alkoxycarbonyl, $C_2$–$C_6$-alkanoylamino, —OR', SR', —$SO_2R'$, —$NHSO_2R'$ or —$NHCO_2R'$; or a 5- or 6-membered aromatic ring containing 1 to 3 heteroatoms selected from the group consisting of oxygen, sulfur and nitrogen, which may be substituted with up to three groups selected from $C_1$–$C_6$-alkyl, $C_1$–$C_6$-alkoxy, halogen, $C_1$–$C_6$-alkylthio, aryl, arylthio, aryloxy, $C_2$–$C_6$-alkoxycarbonyl and $C_2$–$C_6$-alkanoylamino; R is $C_1$ to $C_6$ alkyl and R' is phenyl, naphthyl, or phenyl or naphthyl substituted with one to three groups selected from $C_1$–$C_6$-alkyl, $C_6$–$C_{10}$ aryl, $C_1$–$C_6$-alkoxy or halogen; $R^1$, $R^2$ and $R^4$ may, independently, be hydrogen; and n is 2.

2. The method of claim 1 wherein $R^1$ is hydrogen.

3. The method of claim 2 wherein $R^2$ and $R^3$ are methyl.

4. The method of claim 2 wherein $R^2$ is methyl and $R^3$ is ethyl.

5. The method of claim 3 wherein $R^4$ is methyl or ethyl.

6. The method of claim 4 wherein $R^4$ is methyl.

7. The method of claim 3 wherein $R^6$ is methyl or ethyl.

8. The method of claim 1 wherein the base is non-hydroxide base with a pKa of about 13 or above.

9. The method of claim 8 wherein the base is an amidine base or a guanidine base.

10. The method of claim 8 wherein the base is 1,5-diazabicyclo[4.3.0]non-5-ene (DBN), 1,8-diazabicyclo[5.4.0]undec-7-ene (DBU), or tetramethylguanidine.

* * * * *

UNITED STATES PATENT AND TRADEMARK OFFICE
CERTIFICATE OF CORRECTION

PATENT NO. : 6,897,323 B2
DATED : May 24, 2005
INVENTOR(S) : Boaz et al.

It is certified that error appears in the above-identified patent and that said Letters Patent is hereby corrected as shown below:

Column 16,
Line 56, "$P(OR^8)_3$" should be -- $P(OR^6)_3$ --.

Column 18,
Line 12, after "Claim 3" insert -- or 4 --.

Signed and Sealed this

Nineteenth Day of July, 2005

JON W. DUDAS
*Director of the United States Patent and Trademark Office*